United States Patent [19]
Jung et al.

[11] Patent Number: 5,856,547
[45] Date of Patent: Jan. 5, 1999

[54] ORGANO OMEGA-ALKENYL CYCLOPENTACARBYL SILANE COMPOUNDS

[75] Inventors: Michael Jung; Helmut G. Alt, both of Bayreuth, Germany; M. Bruce Welch, Barltesville, Okla.

[73] Assignee: Phillips Petroleum Company, Bartlesville, Okla.

[21] Appl. No.: 963,113

[22] Filed: Oct. 28, 1997

Related U.S. Application Data

[63] Continuation of Ser. No. 779,497, Jan. 8, 1997, abandoned.

[51] Int. Cl.$^6$ ........................................................... C07F 7/08
[52] U.S. Cl. ............................ 556/465; 556/11; 556/489; 534/15; 526/126; 526/127; 526/129; 526/160; 526/170; 526/241; 526/351; 526/352; 526/348.4

[56] References Cited

U.S. PATENT DOCUMENTS

| | | | |
|---|---|---|---|
| 5,169,818 | 12/1992 | Antberg et al. | 502/159 |
| 5,191,132 | 3/1993 | Patsidis et al. | 585/375 |
| 5,391,789 | 2/1995 | Rohrmann, J. | 556/11 |
| 5,393,911 | 2/1995 | Patsidis et al. | 556/489 |
| 5,406,013 | 4/1995 | Patsidis et al. | 585/375 |
| 5,436,305 | 7/1995 | Alt et al. | 526/160 |
| 5,498,581 | 3/1996 | Welch et al. | 402/102 |
| 5,541,351 | 7/1996 | Patsidis et al. | 556/465 X |
| 5,565,592 | 10/1996 | Patsidis et al. | 556/11 |

FOREIGN PATENT DOCUMENTS

| | | |
|---|---|---|
| 0 586 167 A1 | 9/1994 | European Pat. Off. . |
| 0 604 908 A2 | 9/1994 | European Pat. Off. . |

*Primary Examiner*—Paul F. Shaver
*Attorney, Agent, or Firm*—Carl D. Corvin

[57] ABSTRACT

An (organo) (omega-alkenyl) (cyclopentacarbyl) silane compound is provided. A process that produces an (organo) (omega-alkenyl) (cyclopentacarbyl) silane compound is provided. A process to polymerize olefins, especially ethylene, with a metallocene compound that comprises an (organo) (omega-alkenyl) (cyclopentacarbyl) silane compound is provided.

47 Claims, No Drawings

ORGANO OMEGA-ALKENYL CYCLOPENTACARBYL SILANE COMPOUNDS

This application is a File Wrapper Continuation of application Ser. No. 08/779,497 filed Jan. 8, 1997, now abandoned.

BACKGROUND OF THE INVENTION

In general, this invention is related to the fields of (organo) (omega-alkenyl) (cyclopentacarbyl) silane compounds, processes that produce (organo) (omega-alkenyl) (cyclopentacarbyl) silane compounds, and processes that use (organo) (omega-alkenyl) (cyclopentacarbyl) silane compounds.

The production of polymers that comprise ethylene is a multi-billion dollar enterprise. Many different catalysts can be used to polymerize ethylene. However, very few of these catalysts are of commercial importance. Currently, millions of dollars have been spent on research to make metallocene catalysts more commercially viable and thus, more commercially important. This is because the polymers produced by such metallocene catalysts have properties that currently no other single polymer can reproduce. However, one of the technical problems associated with these metallocene catalysts is that they are homogenous with the polymerization medium. That is, they are soluble in the medium in which the polymerization is conducted. This is a drawback to the use of such metallocene catalysts because most commercially important polymerization processes use heterogenous catalysts. Therefore, in order to make metallocene catalyst more commercially important, heterogenous metallocene catalysts must be produced.

SUMMARY OF THE INVENTION

An object of this invention is to provide an (organo) (omega-alkenyl) (cyclopentacarbyl) silane compound.

Another object of this invention is to provide a process that produces an (organo) (omega-alkenyl) (cyclopentacarbyl) silane compound.

Another object of this invention is to provide a process to polymerize olefins, especially ethylene, with a metallocene compound that contains an (organo) (omega-alkenyl) (cyclopentacarbyl) silane compound.

In accordance with one embodiment of this invention an (organo) (omega-alkenyl) (cyclopentacarbyl) silane compound is provided.

In accordance with another embodiment of this invention a process that produces an (organo) (omega-alkenyl) (cyclopentacarbyl) silane compound is provided. This process comprises (or optionally consists essentially of, or consists of): reacting an (organo) (omega-alkenyl) (monohalogen) silane compound with a (cyclopentacarbyl) metal compound.

In accordance with another embodiment of this invention a process to polymerize olefins, especially ethylene, with a metallocene compound that contains an (organo) (omega-alkenyl) (cyclopentacarbyl) silane compound is provided. This process comprises (or optionally consists essentially of, or consists of): polymerizing monomers into polymers using a metallocene compound that comprises (organo) (omega-alkenyl) (cyclopentacarbyl) silane compound.

The objects and advantages of this invention are further described and defined in the following description and claims. It should be noted that the invention described herein can be practiced without any components or steps not specifically detailed herein.

DETAILED DESCRIPTION OF THE INVENTION

In general, (organo) (omega-alkenyl) (cyclopentacarbyl) silane compounds are produced by reacting an (organo) (omega-alkenyl) (monohalogen) silane compound with a (cyclopentacarbyl) metal compound. Formula One is illustrative of the reaction.

$(R^1)_2C=C(R^1)-(C(R^1)_2)_n-Si(X)(R^2)_2 +$     FORMULA ONE

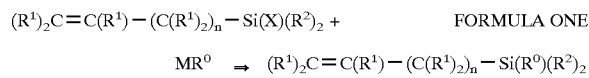

In Formula One the $(R^1)_2C=C(R^1)-(C(R^1)_2)_n-Si(X)(R^2)_2$ compound is the (organo) (omega-alkenyl) (monohalogen) silane compound. In this compound each $R^1$ can be any substituent that does not substantially, and adversely, interfere with any of the processes disclosed herein. For example, each $R^1$ can be a hydrocarbyl having from 1 to about 20 carbon atoms. However, it is preferred that each $R^1$ have from 1 to 10 carbon atoms and it is even more preferred that each $R^1$ have from 1 to 6 carbon atoms. Further examples of $R^1$ are hydrogen, alkyl, aryl, alkoxy, and aryloxy. Currently, it is most preferred if $R^1$ is hydrogen. Also, in this compound, each $R^2$ can be any substituent that does not substantially, and adversely, interfere with any of the processes disclosed herein. For example, each $R^2$ can be a hydrocarbyl having from 1 to about 20 carbon atoms. However, it is preferred that each $R^2$ have from 1 to 10 carbon atoms and it is even more preferred that each $R^2$ have from 1 to 6 carbon atoms. Further examples of $R^2$ are alkyl, aryl, alkoxy, and aryloxy. Currently, it is most preferred if $R^2$ is methyl.

The (organo) (omega-alkenyl) (monohalogen) silane compound can be produced by reacting a alpha-omega diolefin with an (organo) (monohalogen) silane compound using a hydrosilation catalyst. Formula Two is illustrative of the reaction.

$(R^1)_2C=C(R^1)-(C(R^1)_2)_m-(R^1)C=C(R^1)_2 +$     FORMULA TWO

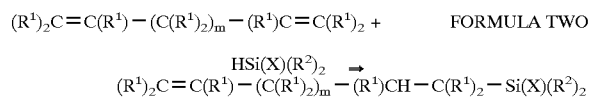

In Formula Two, $R^1$ and $R^2$ have the same meaning as in Formula One. However, m, in Formula Two, is equal to an integer from about 0 to about 28, preferably from about 0 to about 18, and most preferably from 0 to 6. Additionally, X is a halogen, preferably chlorine. Suitable alpha-omega diolefins include, but are not limited to, 1,3 butadiene, 1,4 pentadiene, 1,5 hexadiene, 1,6 heptadiene, 1,7 octadiene, 1,8 nonadiene, and 1,9 decadiene.

Hydrosilation catalysts and reactions are known in the art. For example, the following references could be used to further one's knowledge in this area: U.S. Pat. No. 2,823,218 which discloses a process to produce organo-silane compounds; U.S. Pat. No. 3,419,593 which discloses a process to produce organo-silane compounds; U.S. Pat. No. 3,907,852 which discloses a process to produce silylhydrocarbyl phosphines, wherein section one discloses the addition of silanes to alpha-omega diolefins; and Speier, J. L., Homogeneous Catalysis of Hydrosilation by Transition Metals, ADVANCES IN ORGANOMETALLIC CHEMISTRY, Vol.17, pages 407–447 (1979) which discloses the addition of silanes to substituted-unsaturated-hydrocarbons and unsubstituted-unsaturated-hydrocarbons.

In Formula One, $MR^0$ is the (cyclopentacarbyl) metal compound. In this compound M is a Group I metal. However, preferably M is either lithium, sodium, or potassium. Currently, it is preferred if M is lithium. Also, in this compound, $R^0$ is a (cyclopentacarbyl) group, which can be either substituted or unsubstituted, and which can form a complex with a transition metal to form a metallocene compound. The substituents of the (cyclopentacarbyl) group can be any substituent that does not substantially, and adversely, interfere with any of the processes disclosed herein. Examples of (cyclopentacarbyl) groups are substituted and unsubstituted cyclopentadiene groups, substituted and unsubstituted indenyl groups, substituted and unsubstituted tetrahydroindenyl groups, and substituted and unsubstituted fluorenyl groups.

In Formula One, n is an integer from about 2 to about 30, preferably from about 2 to about 20 and most preferably 2 to 8.

In general, the reaction of the (organo) (omega-alkenyl) (monohalogen) silane compound with a (cyclopentacarbyl) metal compound to produce an (organo) (omega-alkenyl) (cyclopentacarbyl) silane compound is conducted at any suitable temperature and pressure. Currently, a temperature of about −80° C. to about 160° C. and a pressure of about 0 to about 100 atmospheres are preferred. However, a temperature of about −50° C. to about 60° C. and a pressure of about 1 atmosphere are more preferred. The molar ratio of the (organo) (omega-alkenyl) (monohalogen) silane compound to the (cyclopentacarbyl) metal compound can be any suitable ratio. Currently, a molar ratio of 1 to 1 is preferred.

Once the (organo) (omega-alkenyl) (cyclopentacarbyl) silane compound is produced it can be used to produce metallocene compounds wherein the (organo) (omega-alkenyl) (cyclopentacarbyl) silane compound is, at least, one of the ligands of the metallocene compound. Various methods are known in the art to bind a ligand to a transition metal in order to produce a metallocene compound. For example, the following references can be consulted: U.S. Pat. Nos. 5,436,305; 5,498,581; 5,565,592; and European Application 524,624 (the entire disclosures of which are hereby incorporated by reference). In general, however, metallocene compounds that contain an (organo) (omega-alkenyl) (cyclopentacarbyl) silane compound can be prepared by reacting the (organo) (omega-alkenyl) (cyclopentacarbyl) silane compound with alkali metal alkyl to produce a ligand salt that is then reacted with a transition metal compound to yield the metallocene compound.

These metallocene compounds can be used to polymerize various olefins. The particular polymerization conditions employed using these compounds can vary depending upon the particular results desired. Usually these compounds are used with organoaluminoxane compounds, such as, for example, methylaluminoxane, to form better polymerization catalysts. The ratio of the transition metal to the organoaluminoxane composition can vary widely depending upon the particular composition selected and the results desired. Typically, the atomic ratio of aluminum in the organoaluminoxane composition to the transition metal is in the range of about 1/1 to about 20000/1, preferably about 15/1 to about 5000/1, and more preferably about 100/1 to about 1000/1.

Examples of some monomers for polymerization include ethylene and alpha-olefins having 3 to 20 carbon atoms, such as propylene, 1-butene, 3-methyl-1-butene, 3-methyl-1-pentene, 3 ethylene-1-hexene, 1-hexene, 4-methyl-1-pentene, 1-octene, 1-hexadecene, cyclopentene, norborene, styrene, 4-methyl styrene, vinyl cyclohexane, butadiene, and the like and mixtures thereof.

The present invention is particularly useful in slurry type polymerizations since it allows one to carry out such polymerizations more effectively than has heretofore been possible. A particularly preferred type of slurry polymerization involves the continuous loop reactor type polymerization wherein monomer, catalyst, and diluent, if employed, are continuously added to the reactor as needed and polymer product is continuously or at least periodically removed. Generally in such processes, ethylene is polymerized in the presence of a suitable liquid diluent, a higher alpha-olefin comonomer, and optionally, hydrogen. The polymerization temperature can vary over the range which will allow for slurry polymerization. Often slurry polymerization will be conducted at a temperature in the range of about 50° C. to about 100° C., although higher and lower temperatures can be used.

One of the benefits of this invention is that the metallocene compound is that during polymerization the metallocene compound is incorporated into the polymer chain thereby forming a heterogenous metallocene catalyst. As discussed above, this is a very important result because it increases the commercial importance of metallocene compounds used for polymerization. For example, a heterogenous metallocene catalyst can be formed by prepolymerizing these metallocene catalysts with a monomer, such as, for example, ethylene, to form a prepolymer supported metallocene compound. Examples of such techniques are disclosed in U.S. Pat. No. 5,498,581, the entire disclosure of which is hereby incorporated by reference.

The following examples are provided to further illustrate this invention. However, the invention should not be construed to be limited to the particular embodiments in these examples.

EXAMPLES

All examples were carried out using standard Schlenk techniques with the exclusion of oxygen and air moisture under argon. The solvents were dried over either: (a) Na/K alloy for ether, hexane, pentane, tetrahydrofuran, and toluene; (b) $P_4O_{10}$ for methylene chloride; or (c) magnesium for methanol; and then distilled under argon.

Example One

Preparation of an (Organo) (Monohalogen) (Omega-Alkenyl) Silane Compound

Eighty mL (676 mmol) of 1,5 hexadiene, which is an alpha-omega diolefin compound, and a spatula tip of bis (1,3 diphenyl-3-hydroxy-1-butynyl) platinum, which is a hydrosilation catalyst compound, were mixed in a container to form a first mixture. Forty mL of dimethylchlorosilane, which is an (organo) (monohalogen) silane compound, was added dropwise to said first mixture, over a three hour period, to produce a second mixture. This second mixture was then stirred for two hours. This second mixture was then distilled using a high vacuum ($10^{-2}$ torr) to produce a product. This product was (dimethyl) (chloro) (5-hexenyl) silane, which is an (organo) (monohalogen) (omega-alkenyl) silane compound.

Example Two

Preparation of an (Organo) (Omega-Alkenyl) (Cyclopentacarbyl) Silane Compound Ten mL (85.7 mmol) of indene, which is a (cyclopentacarbyl) compound, was added to a container that contained 150 mL of diethyl ether and 15 mL of tetrahydrofuran to form a first mixture. This first mixture was then reacted with 53.6 mL (85.7 mmol) of n-butyllithium (1.6M in hexane) to form indenyllithium, which is a (cyclopentacarbyl) metal compound. This reaction took place at −78° C. A yellow solution was formed. This yellow solution was then stirred at room temperature (about 25° C.) for four hours and then cooled again to about −78° C. An equivalent quantity of (dimethyl) (chloro) (5-hexenyl) silane compound, prepared in Example One, was added dropwise to the yellow solution to form a second mixture. This second mixture was then stirred overnight at room temperature (about 25 ° C.). Thereafter, this second mixture was then hydrolyzed with 50 mL of water to form two phases, an organic phase and a water phase. The organic phase was dried over sodium sulfate and then the solvent was evaporated under a vacuum to produce a third mixture. This third mixture was then distilled using a high vacuum ($10^{-2}$ torr) to obtain a product. The product obtained was (dimethyl) (5-hexenyl) (1-indene) silane, which is an (organo) (omega-alkenyl) (cyclopentacarbyl) silane compound.

Example Three

Preparation of a Metallocene Compound That Contains an (Organo) (Omega-Alkenyl) (Cyclopentacarbyl) Silane Compound Example 3-1

Ten mmol of (dimethyl) (5-hexenyl) (1-indene) silane, prepared in Example Two, was mixed with 60 mL of diethyl ether to form a first mixture. This first mixture was then reacted with 6.25 mL of butyllithium (1.6M solution in hexane) to form a second mixture. This second mixture was stirred for four hours. Thereafter 2.58 grams (10 mmol) of (9-fluorenyl) (dimethyl) (chloro) silane, which is a (cyclopentacarbyl) (organo) (monohalogen) silane compound, was added to the second mixture to form a third mixture. This third mixture was then hydrolyzed with 50 mL of water to form an organic phase and a water phase. The organic phase was then dried over sodium sulfate and thereafter evaporated to form a first product. This first product was (1-(3-(hex-5-enyl) (dimethyl) silyl) indenyl) (dimethyl) (9-fluorenyl) silane.

One gram of this first product was mixed with 40 mL of diethyl ether to form a fourth mixture. This fourth mixture was stirred with 2 equivalents of n-butyllithium (1.6M in hexane) for about eight hours at room temperature (about 25 ° C.) to form a fifth mixture. Thereafter, an equivalent of zirconium tetrachloride was added to the fifth mixture and stirred overnight to form a second product. This second product was (1-(3-(hex-5-enyl) (dimethyl) silyl) indenyl) (dimethyl) (9-fluorenyl) silane zirconium dichloride, a metallocene compound.

Example 3-2

Ten mmol of (dimethyl) (5-hexenyl) (1-indene) silane, prepared in Example Two, was mixed with 60 mL of diethyl ether and 6 mL of hexamethylphosphoric acid triamide to form a first mixture. This first mixture was then reacted with 6.25 mL of butyllithium (1.6M solution in hexane) to form a second mixture. This second mixture was stirred for four hours. Thereafter 2.73 grams (10 mmol) of 1-bromo-2-(9-fluorenyl)ethane, which is a (cyclopentacarbyl) (monohalogen) hydrocarbon compound, was added to the second mixture to form a third mixture. This third mixture was stirred for three days. This third mixture was then hydrolyzed with water to form an organic phase and a water phase. The organic phase was then dried over sodium sulfate and thereafter evaporated to form a first product. This first product was (1-(3-(hex-5-enyl) (dimethyl) silyl) indenyl) (2-(9-fluorenyl)) ethane.

One gram of this first product was mixed with 40 mL of diethyl ether to form a fourth mixture. This fourth mixture was stirred with 2 equivalents of n-butyllithium (1.6M in hexane) for about eight hours at room temperature (about 25° C.) to form a fifth mixture. Thereafter, an equivalent of zirconium tetrachloride was added to the fifth mixture and stirred overnight to form a second product. This second product was (1-(3-(hex-5-enyl) (dimethyl) silyl) indenyl) (2-(9-fluorenyl)) ethane zirconium dichloride, a metallocene compound.

Example Four

Polymerization of Ethylene With a Metallocene Compound That Contains an (Organo) (Omega-Alkenyl) (Cyclopentacarbyl) Silane Compound Example 4-1

About 10 mg of (1-(3-(hex-5-enyl) (dimethyl) silyl) indenyl) (dimethyl) (9-fluorenyl) silane zirconium dichloride, prepared in Example 3-1, was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.6 \times 10^{31\ 6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 72 grams of polyethylene was recovered.

Example 4-2

About 10 mg of (1-(3-(hex-5-enyl) (dimethyl) silyl) indenyl) (2-(9-fluorenyl)) ethane zirconium dichloride, prepared in Example 3-2, was mixed with 10 mL of methylaluminoxane (30 weight percent in toluene) to form a catalyst complex and then diluted with 10 mL of toluene. The polymerization of ethylene was carried out in a 1 L Buechi laboratory autoclave. The autoclave was filled with 500 mL of pentane and 7 mL of methylaluminoxane. An amount (about $1.3 \times 10^{-6}$ mol) of catalyst complex was then added to the autoclave. The autoclave thermostat was then set to 60° C. and a constant ethylene pressure of 10 bar was applied. The reactor was stirred at 800 rpm. The polymerization was stopped after one hour. About 80 grams of polyethylene was recovered.

Example Five

Polymerization of Ethylene With a Metallocene Compound That Contains an (Organo) (Omega-Alkenyl) (Cyclopentacarbyl) Silane Compound to Form a Heterogenous Catalyst Complex Example 5-1

In a Schlenk tube (1-(3-(hex-5-enyl) (dimethyl) silyl) indenyl) (dimethyl) (9-fluorenyl) silane zirconium dichloride, prepared in Example 3-1, was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

Example 5-2

In a Schlenk tube (1-(3-(hex-5-enyl) (dimethyl) silyl) indenyl) (2-(9-fluorenyl)) ethane zirconium dichloride zirconium dichloride, prepared in Example 3-2, was mixed with methylaluminoxane and toluene to form a catalyst complex. This catalyst complex was then exposed to an ethylene pressure of 0.4 to 0.6 bar to incorporate the catalyst complex into an ethylene polymer chain thereby forming a heterogenous metallocene catalyst.

That which is claimed:

1. A composition of matter having the following formula

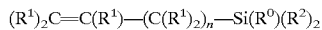

wherein $R^0$ is a (cyclopentacarbyl) group; and wherein each $R^1$ is a hydrocarbyl having from 1 to about 20 carbon atoms; and wherein each $R^2$ is a hydrocarbyl having from 1 to about 20 carbon atoms and is selected from the group consisting of alkyls, aryls, alkoxy, and aryloxy; and wherein n is an integer from about 2 to about 30; and where said composition of matter is produced by a process comprising reacting a composition of matter having the following formula

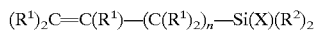

with a composition of matter having the following formula $MR^0$ wherein $R^0$, $R^1$, $R^2$, and n are as earlier defined and M is a Group I metal.

2. A composition according to claim 1 wherein $R^0$ is selected from the group consisting of substituted and unsubstituted cyclopentadiene groups, substituted and unsubstituted indenyl groups, substituted and unsubstituted tetrahydroindenyl groups, and substituted and unsubstituted fluorenyl groups.

3. A composition according to claim 2 wherein $R^0$ is selected from the group consisting of substituted and unsubstituted cyclopentadiene groups and substituted and unsubstituted indenyl groups.

4. A composition according to claim 3 wherein each $R^1$ has from 1 to 10 carbon atoms.

5. A composition according to claim 4 wherein each $R^1$ has from 1 to 6 carbon atoms.

6. A composition according to claim 5 wherein each $R^1$ is selected from the group consisting of hydrogen, alkyl, aryl, alkoxy, and aryloxy.

7. A composition according to claim 6 wherein each $R^1$ is hydrogen.

8. A composition according to claim 7 wherein each $R^2$ has from 1 to 10 carbon atoms.

9. A composition according to claim 8 wherein each $R^2$ has from 1 to 6 carbon atoms.

10. A composition according to claim 9 wherein each $R^2$ is methyl.

11. A composition according to claim 10 wherein n is from about 2 to about 20.

12. A composition according to claim 11 wherein n is from 2 to 8.

13. A process to produce a composition of matter having the following formula

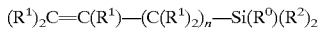

wherein $R^0$ is a (cyclopentacarbyl) group; and wherein each $R^1$ is a hydrocarbyl having from 1 to about 20 carbon atoms; and wherein each $R^2$ is a hydrocarbyl having from 1 to about 20 carbon atoms and is selected from the group consisting of alkyls, aryls, alkoxy, and aryloxy; and wherein n is an integer from about 2 to about 30;

said process comprising reacting a composition of matter having the following formula

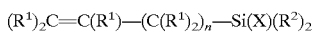

with a composition of matter having the following formula

wherein $R^0$, $R^1$, $R^2$, and n are as earlier defined and M is a Group I metal.

14. A process according to claim 13 wherein $R^0$ is selected from the group consisting of substituted and unsubstituted cyclopentadiene groups, substituted and unsubstituted indenyl groups, substituted and unsubstituted tetrahydroindenyl groups, and substituted and unsubstituted fluorenyl groups.

15. A composition according to claim 14 wherein $R^0$ is selected from the group consisting of substituted and unsubstituted cyclopentadiene groups and substituted and unsubstituted indenyl groups.

16. A process according to claim 15 wherein each $R^1$ has from 1 to 10 carbon atoms.

17. A process according to claim 16 wherein each $R^1$ has from 1 to 6 carbon atoms.

18. A process according to claim 17 wherein each $R^1$ is selected from the group consisting of hydrogen, alkyl, aryl, alkoxy, and aryloxy.

19. A process according to claim 18 wherein each $R^1$ is hydrogen.

20. A process according to claim 19 wherein each $R^2$ has from 1 to 10 carbon atoms.

21. A process according to claim 20 wherein each $R^2$ has from 1 to 6 carbon atoms.

22. A process according to claim 21 wherein each $R^2$ is methyl.

23. A process according to claim 22 wherein n is from about 2 to about 20.

24. A process according to claim 23 wherein n is from 2 to 8.

25. A process according to claim 24 wherein M is selected from the group consisting of lithium, sodium, or potassium.

26. A process according to claim 25 wherein M is lithium.

27. A process according to claim 26 wherein said reacting is conducted at a temperature from about −80° C. to about 160° C. and a pressure of from about 0 to about 100 atmospheres.

28. A process according to claim 27 wherein said reacting is conducted at a temperature from about −50° C. to about 60° C.

29. A process of polymerizing monomers into polymers using a metallocene compound that comprises at least one ligand wherein said ligand has the following formula

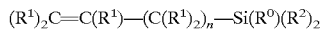

wherein $R^0$ is a (cyclopentacarbyl) group; and wherein each $R^1$ is a hydrocarbyl having from 1 to about 20 carbon atoms; and wherein each $R^2$ is a hydrocarbyl having from 1 to about 20 carbon atoms; and wherein n is an integer from about 2 to about 30; and where said ligand is produced by a process comprising reacting a composition of matter having the following formula

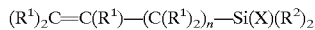

with a composition of matter having the following formula $MR^0$ wherein $R^0$, $R^1$, $R^2$, and n are as earlier defined and M is a Group I metal.

30. A process according to claim 29 wherein $R^0$ is selected from the group consisting of substituted and unsubstituted cyclopentadiene groups, substituted and unsubstituted indenyl groups, substituted and unsubstituted tetrahydroindenyl groups, and substituted and unsubstituted fluorenyl groups.

31. A process according to claim 30 wherein $R^0$ is selected from the group consisting of substituted and unsubstituted cyclopentadiene groups, and substituted and unsubstituted indenyl groups.

32. A process according to claim 31 wherein each $R^1$ has from 1 to 10 carbon atoms.

33. A process according to claim 32 wherein each $R^1$ has from 1 to 6 carbon atoms.

34. A process according to claim 33 wherein each $R^1$ is selected from the group consisting of hydrogen, alkyl, aryl, alkoxy, and aryloxy.

35. A process according to claim 34 wherein each $R^1$ is hydrogen.

36. A process according to claim 35 wherein each $R^2$ has from 1 to 10 carbon atoms.

37. A process according to claim 36 wherein each $R^2$ has from 1 to 6 carbon atoms.

38. A process according to claim 37 wherein each $R^2$ is methyl.

39. A process according to claim 38 wherein n is from about 2 to about 20.

40. A process according to claim 39 wherein n is from 2 to 8.

41. A process according to claim 40 wherein said monomers comprise ethylene.

42. A process according to claim 41 wherein said monomers consist essentially of ethylene.

43. A process according to claim 42 wherein said monomers consist of ethylene.

44. A process according to claim 43 wherein said monomers comprise ethylene and olefins having from 3 to 20 carbon atoms.

45. A process according to claim 44 wherein said monomers comprise ethylene and olefins selected from the group consisting of propylene, 1-butene, 3-methyl-1-butene, 3-methyl-1-pentene, 3 ethylene-1-hexene, 1-hexene, 4-methyl-1-pentene, 1-octene, 1-hexadecene, butadiene, and mixtures thereof.

46. A process according to claim 44 wherein said monomers comprise ethylene and olefins selected from the group consisting of cyclopentene, norborene, styrene, 4-methyl styrene, vinyl cyclohexane, and mixtures thereof.

47. A process according to claim 44 wherein said monomers comprise ethylene and 1-hexene.

* * * * *